(12) United States Patent
Talamonti et al.

(10) Patent No.: US 11,751,784 B2
(45) Date of Patent: Sep. 12, 2023

(54) SYSTEMS AND METHODS FOR DETECTING DROWSINESS IN A DRIVER OF A VEHICLE

(71) Applicant: Ford Global Technologies, LLC, Dearborn, MI (US)

(72) Inventors: Walter Talamonti, Canton, MI (US); Ali Hassani, Ann Arbor, MI (US); Aniruddh Ravindran, Sunnyvale, CA (US)

(73) Assignee: Ford Global Technologies, LLC, Dearborn, MI (US)

( * ) Notice: Subject to any disclaimer, the term of this patent is extended or adjusted under 35 U.S.C. 154(b) by 365 days.

(21) Appl. No.: 16/822,540

(22) Filed: Mar. 18, 2020

(65) Prior Publication Data

US 2021/0290134 A1 Sep. 23, 2021

(51) Int. Cl.
*A61B 5/18* (2006.01)
*A61B 5/11* (2006.01)
(Continued)

(52) U.S. Cl.
CPC .............. *A61B 5/18* (2013.01); *A61B 5/0022* (2013.01); *A61B 5/1103* (2013.01);
(Continued)

(58) Field of Classification Search
CPC ...... G08B 21/06; G08B 21/0453; A61B 5/18; A61B 5/024; A61B 5/6893;
(Continued)

(56) References Cited

U.S. PATENT DOCUMENTS 8,872,640 B2 * 10/2014 Horseman .............. B60K 28/06
340/425.5
2011/0208675 A1 * 8/2011 Shoureshi .............. G06N 5/048
706/2
(Continued)

FOREIGN PATENT DOCUMENTS

JP 2018518205 A 7/2018

OTHER PUBLICATIONS

Balandong, et al., "A Review on EEG-Based Automatic Sleepiness Detection Systems for Driver", IEEE Access, Mar. 2018 (15 pages).

*Primary Examiner* — Daniel Previl
(74) *Attorney, Agent, or Firm* — Frank Lollo; Eversheds Sutherland (US) LLP (57) ABSTRACT

Example embodiments described in this disclosure are generally directed to detecting drowsiness in a driver of a vehicle. In an example method, a driver drowsiness detection system receives a motor cortex signal from a brain activity monitoring element attached to the driver. The brain activity monitoring element can be a cortical implant, for example. The driver drowsiness detection system evaluates the motor cortex signal to identify an anatomical part of the driver (eyes, for example) that is associated with a brain activity. The driver drowsiness detection system then uses a drowsiness detection device placed in the vehicle for evaluating a physical activity of the anatomical part. The evaluation may be carried out by using a camera directed upon the driver's eyes, for example. The driver drowsiness detection system determines a drowsiness state of the driver based on the evaluation and assigns a sleep risk score.

17 Claims, 5 Drawing Sheets

(51) Int. Cl.
  *A61B 5/00* (2006.01)
  *A61B 5/16* (2006.01)
(52) U.S. Cl.
  CPC ............ *A61B 5/1114* (2013.01); *A61B 5/162* (2013.01); *A61B 5/4809* (2013.01); *A61B 5/6803* (2013.01); *A61B 5/6893* (2013.01); *A61B 5/7275* (2013.01); *A61B 5/746* (2013.01); *A61B 2562/0247* (2013.01)
(58) Field of Classification Search
  CPC ............ A61B 2560/0242; A61B 3/113; A61B 5/0077; A61B 5/0205; A61B 5/02405; A61B 5/0531; A61B 5/4809; A61B 5/4812; A61B 5/7264; A61B 5/7278; A61B 5/7455; A61B 5/746; A61B 5/0476; A61B 5/0533; B60W 2040/0827; B60W 2540/221; B60W 2540/26; B60W 2710/18; B60W 30/09; B60W 2050/143; B60W 2540/30; B60W 2040/0818; B60W 2040/0872; B60W 2420/42; B60W 2422/00; B60W 2540/22; B60W 2554/00; B60W 2556/50; B60W 2710/20; B60W 2720/10; B60W 30/08; B60W 30/085; B60W 30/095; B60W 30/12; B60W 30/14; B60W 30/143; B60W 30/18036; B60W 40/08; B60W 50/087; B60W 50/14; B60W 50/16; B60W 2050/0028; B60W 2050/0089; B60W 2554/4029; B60W 50/00; B60W 50/0098; B60K 28/06; B60K 28/066; B60K 28/02; G08G 1/16; G08G 1/166; G08G 1/167; G08G 1/168; G08G 1/096775; G08G 1/164; A61M 2021/0083; A61M 2021/0027; A61M 2021/0044; A61M 21/00; A61M 21/02; A61M 2205/3375; A61M 2205/505; A61M 2230/06; A61M 2230/63; B60R 11/02; B60R 21/00; B60R 21/015; B60R 11/04; B60N 2002/981; B60N 2/0276; B60N 2/90; B60N 2/002; A47C 7/62; B60H 1/00742; B60Q 9/00; B60T 7/12; G01C 21/3484; G01C 21/36; G05D 1/0061; G05D 1/0088; G06K 9/00845; G06K 9/00288; G06K 9/00805; G06K 9/00838; G06K 9/2027; G05B 13/0265; G16H 50/20; H04B 1/3877; H04M 1/0264; H04M 1/04; H04M 1/6075; H04M 1/64; H04M 1/72527; H04M 1/72577; H04M 2250/10; H04M 2250/52; H04N 5/77
  USPC ...... 340/576, 425.5, 573.1, 575, 574, 573.6, 340/691.6, 3.1, 5.82
  See application file for complete search history.

(56) References Cited

U.S. PATENT DOCUMENTS

| | | | |
|---|---|---|---|
| 2017/0071525 A1* | 3/2017 | Lin | ............... A61B 5/0476 |
| 2018/0037236 A1* | 2/2018 | Yamaguchi | ............... A47C 7/62 |
| 2019/0121356 A1* | 4/2019 | Migneco | ............... A61B 5/7264 |
| 2020/0029880 A1* | 1/2020 | Katnani | ............... A61B 5/4064 |

* cited by examiner

SYSTEMS AND METHODS FOR DETECTING DROWSINESS IN A DRIVER OF A VEHICLE

BACKGROUND

A concern in traffic safety is driver behavior, particularly driver behaviors associated with distracted driving and drowsiness. Vehicle manufacturers have addressed such types of driver behaviors by offering driver state monitoring systems. A typical driver state monitoring system monitors various physical characteristics of a driver in order to continuously assess the driver's alertness. One among the various physical characteristics that are monitored by the driver state monitoring system in order to identify drowsiness, is a condition of the driver's eyes. Typically, the eyelids of a sleepy driver tend to be either droopy, partially closed, or fully closed. When such an eyelid condition is detected, the driver state monitoring system may provide an audible alarm and/or provide a vibration in the steering wheel of the vehicle so as to awaken the driver.

These kinds of driver state monitoring systems may be effective in determining that a driver appears to be inattentive, but may not be effective in differentiating between a driver staring blankly out of the windshield of a vehicle and a tired driver who is falling asleep. In some cases, a "blank stare" may result in the eyes of the driver appearing to be looking ahead normally and the hands of the driver may continue to grip a steering wheel of the vehicle with sufficient pressure so as to mislead the driver state monitoring system into concluding that the driver is engaged and fully alert, rather than being inattentive. On the other hand, if the driver were to loosen his/her grip on the steering wheel while staring ahead normally, the driver state monitoring system may conclude that the driver is about to fall sleep.

The inability of traditional driver state monitoring systems to accurately detect an onset of sleep in a driver of a vehicle may turn out to be even more problematic when the vehicle is a fully autonomous vehicle and it is not necessary for a person to place his/her hands on the steering wheel of the vehicle. More particularly, some traditional driver state monitoring systems may disable monitoring of touch inputs when the vehicle is a fully autonomous vehicle, and may also reduce certain functionalities of a camera if installed in the vehicle for monitoring a person's eyes. In such a scenario, an occupant of the autonomous vehicle seated at the traditional driver seat may fall asleep, thereby rendering him/her unable to react to any unusual driving situation that the autonomous vehicle cannot handle.

It is therefore desirable to provide additional solutions to monitor driver state.

BRIEF DESCRIPTION OF THE DRAWINGS

A detailed description is set forth below with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

In terms of a general overview, the disclosure is directed to systems and methods for detecting drowsiness of a driver of a vehicle. In an example method, a driver drowsiness detection system receives a motor cortex signal from a brain activity monitoring element attached to the driver. The brain activity monitoring element can be a cortical implant, for example. The driver drowsiness detection system evaluates the motor cortex signal to identify an anatomical part of the driver (eyes, for example) that is associated with a brain activity. The driver drowsiness detection system then uses a drowsiness detection device placed in the vehicle for evaluating a physical activity of the anatomical part. The evaluation may be carried out by using a camera directed upon the driver's eyes, for example. The driver drowsiness detection system determines a drowsiness state of the driver based on the evaluation and assigns a sleep risk score.

Illustrative Embodiments

The disclosure will be described more fully hereinafter with reference to the accompanying drawings, in which example embodiments of the disclosure are shown. This disclosure may, however, be embodied in many different forms and should not be construed as limited to the example embodiments set forth herein. It will be apparent to persons skilled in the relevant art that various changes in form and detail can be made to various embodiments without departing from the spirit and scope of the present disclosure. Thus, the breadth and scope of the present disclosure should not be limited by any of the above-described example embodiments but should be defined only in accordance with the following claims and their equivalents. The description below has been presented for the purposes of illustration and is not intended to be exhaustive or to be limited to the precise form disclosed. It should be understood that alternate implementations may be used in any combination desired to form additional hybrid implementations of the present disclosure. For example, any of the functionality described with respect to a particular device or component may be performed by another device or component. Furthermore, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments.

Certain words and phrases are used herein solely for convenience and such words and terms should be interpreted as referring to various objects and actions that are generally understood in various forms and equivalencies by persons of ordinary skill in the art. For example, word "driver" as used herein may be equally applicable to any occupant of a vehicle. The word "vehicle" as used in this disclosure can pertain to any one of various types of vehicles such as cars, vans, sports utility vehicles, trucks, electric vehicles, gasoline vehicles, hybrid vehicles, and autonomous vehicles. The word "biometrics" as used in this disclosure generally refers to various parameters of a human body that may be used to identify a physical condition, such as a sleeping condition or an alert condition. The word "information" as used herein can pertain to data, signals, communications (for example, messages), sensor outputs, and other such items that can be processed by processing circuitry for carrying out various operations. Words such as "component" and "element" may be used interchangeably. It should also be understood that the word "example" as used herein is intended to be non-exclusionary and non-limiting in nature.

Figure 1:
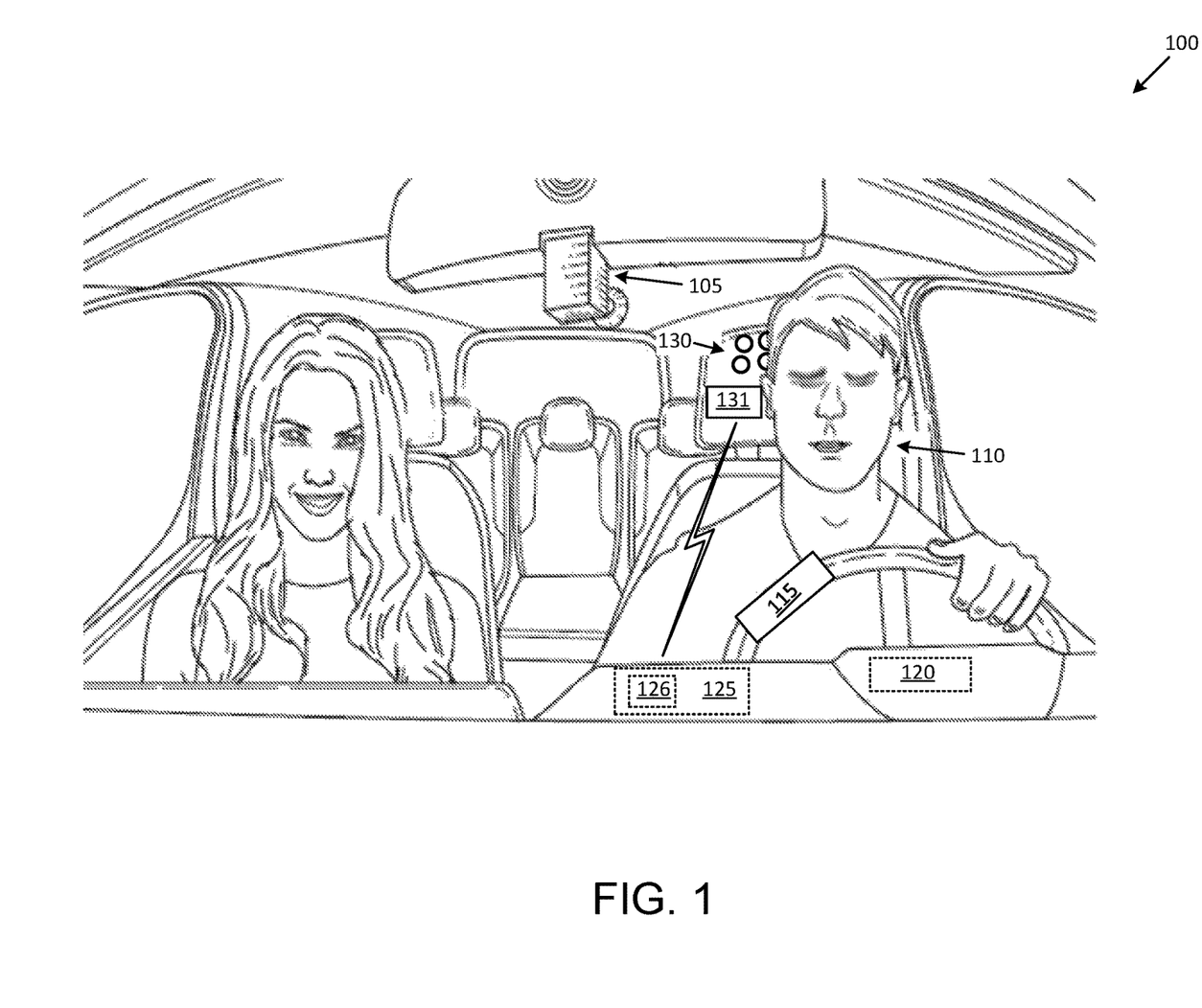
FIG. 1 illustrates an example implementation of a driver drowsiness detection system in accordance with a first embodiment of the disclosure.

FIG. 1 illustrates an example implementation of a driver drowsiness detection system 100 in accordance with a first embodiment of the disclosure. The driver drowsiness detection system 100 may be used to detect a drowsiness state of a driver 110 of a vehicle and to assign a sleep risk score based on the drowsiness state. Though the following description is directed at the driver 110, it must be understood that the description is equally applicable to any occupant of a vehicle. For example, in some instances, the vehicle can be an autonomous vehicle and all the occupants of the autonomous vehicle are passengers. In such a situation, particularly when the autonomous vehicle is a ride share vehicle and the passengers do not know each other, it may be disconcerting for a first passenger seated in a back seat to see a second passenger sitting in a driver seat of the vehicle with eyes completely closed. Accordingly, the driver drowsiness detection system 100 may be used to detect a drowsiness state of any one or more occupants of the vehicle.

The driver drowsiness detection system 100 may be broadly classified as having a first detection subsystem, a second detection subsystem, and a processing system 125. The first detection subsystem can include one or more sensing elements that are attached to the driver 110 for purposes of detecting brain activity. A few examples of such sensing elements may include a cortical implant, an electric field encephalography sensor, an electroencephalography sensor, a near infra-red spectroscopy sensor, and other available active or passive brain activity monitoring systems. The sensing elements may be attached or coupled to the driver 110 in various ways. In some cases, a sensing element may be placed in direct contact with the driver 110. In some other cases, a sensing element may be coupled to the driver 110 via an infrared link, an ultrasonic link, or a wireless link, for example, and configured to capture various brain activity signals such as, for example, an electroencephalogram (EEG) signal or an electroencephalogram (ECG) signal.

The brain activity signals may be used by the first detection subsystem to identify a physical action that the driver 110 intends to perform and/or certain a physical action that the driver 110 may not be about to perform. For example, in one case, an overactive EEG or ECG signal may provide an indication that the driver 110 is reacting to an unexpected traffic situation and intends to hit the brakes. In another case, a restful EEG or ECG signal may provide an indication that the driver 110 is not reacting to an unexpected traffic situation and may not hit the brakes in time to avoid an accident.

In one example implementation, a motor cortex signal of the driver 110 may be evaluated by the processing system 125 to identify an anatomical part of the driver 110 that is associated with brain activity indicating drowsiness. For example, the motor cortex signal may pertain to a certain type of brain activity taking place in the occipital lobe of the brain of the driver 110. The brain activity may indicate a condition of the eyes of the driver 110, such as, for example, a drowsiness condition. Signals from one or more sensors of the second detection subsystem, such as an imaging apparatus 105, for example, may then be used by the processing system 125 to evaluate the eyes of the driver 110 and confirm that the driver 110 is drowsy.

In the example implementation shown in FIG. 1, the first detection subsystem includes a brain activity monitoring element in the form of a headrest cortical sensor system 130 having a set of sensing elements located in a headrest of the vehicle. The set of sensing elements may be arranged to detect a motor cortex signal in a cranial area of the driver 110. The set of sensing elements may include various types of transducers that may detect the motor cortex signal by direct contact with the cranium of the driver 110, or wirelessly by communicating with components attached to the cranium of the driver 110. The set of sensing elements may be coupled to a wireless transceiver 131 that wirelessly communicates with a wireless transceiver 126 in the processing system 125.

The second detection subsystem may include various sensing elements such as, for example, the imaging apparatus 105, a facial recognition system 120, and one or more biometric sensors (such as, an example biometric sensor 115). The second detection subsystem may also include sensing elements that provided information on actions carried out by the driver 110 upon various parts of the vehicle such as, for example, a braking action carried out by depressing a brake pedal in the vehicle, a swerving action carried out by rotating the steering wheel of the vehicle, or an acceleration action carried out by depressing an accelerator of the vehicle.

The imaging apparatus 105 can be mounted on any of various parts of the vehicle having a field of view that encompasses at least a portion of a face of the driver 110, particularly the eyes of the driver 110. The imaging apparatus 105 in this example illustration is mounted upon a rear-view mirror of the vehicle and is arranged to capture one or more images of the eyes of the driver 110. In some cases, the imaging apparatus 105 can be a video camera that captures real-time video of at least the eyes of the driver 110. In some other cases, the imaging apparatus 105 can be a digital camera that captures digital images of at least the eyes of the driver 110. The digital images may be captured on a repetitive basis, an intermittent basis, and/or a random basis. The real-time video and/or digital images are conveyed to the processing system 125 for processing in order to detect an eyelid status of the driver 110. An eyelid status, such as, for example, an open condition, a drooping condition, a partially closed condition, or a fully closed condition, may provide an indication of a drowsiness state of the driver 110.

The facial recognition system 120 can be mounted on any of various parts of the vehicle having a field of view that encompasses a face of the driver 110. The facial recognition system 120 in this example illustration is mounted upon an instrument panel of the vehicle and is arranged to capture images of the face of the driver 110 (digital images and/or video). The images may be conveyed to the processing system 125 for processing in order to analyze various facial features of the driver 110. Facial features such as a drooping mouth, a slack jaw, and/or an angular orientation may provide an indication of a drowsiness state of the driver 110.

The biometric sensor 115 can include one or more of various types of devices that may be mounted on various parts of the vehicle and used to detect various types of physical conditions of the driver 110 for purposes of evaluating a drowsiness state of the driver 110. The biometric sensor 115 in this example illustration is a pressure sensor that senses a placement of the hands of the driver 110 upon the steering wheel, and/or an intensity of a hand grip of the driver 110 upon the steering wheel. In another example embodiment, the biometric sensor 115 can be a body sensor that is located in a driver seat occupied by the driver 110. The body sensor may measure various biometric parameters of the driver 110, such as, for example, blood pressure, heart rate, and breathing pattern. The body sensor may incorporate various types of technologies, such as, for example, infra-red technology, green light technology, radio-frequency (RF) technology, and/or pressure transducer technology.

One example of the use of infra-red technology is for temperature measurements and distance measurements. One example of the use of green-light technology is in fitness monitoring devices such as a Fitbit® activity tracker where a pair of LEDs shine green light that measures minute changes in the color characteristics of blood flowing through a human body. The color characteristics typically vary in correspondence to a blood pumping action of the heart and can be used to determine parameters such as pulse rate and heartbeat.

In an example scenario, the processing system 125 of the driver drowsiness detection system 100 may evaluate a motor cortex signal that is detected by the set of sensing elements of the first detection subsystem and identify, for example, a certain type of brain activity taking place in the occipital lobe of the brain of the driver 110. The brain activity may indicate a drowsiness condition associated with the eyes of the driver 110. The processing system 125 may then communicate with the imaging apparatus 105 that is a part of the second detection subsystem for obtaining images of the eyes of the driver 110. The images may be evaluated by the processing system 125 to confirm that the driver 110 is drowsy.

In another example scenario, the driver drowsiness detection system 100 may evaluate a motor cortex signal that is detected by the set of sensing elements of the first detection subsystem and identify, for example, a certain type of brain activity taking place in a portion of the brain pertaining to the jaw of the driver 110. The processing system 125 may then communicate with the facial recognition system 120 of the second detection subsystem to obtain images of the jaw of the driver 110. The images may be evaluated by the processing system 125 to confirm that the driver 110 is drowsy.

In yet another example scenario, the processing system 125 may evaluate a motor cortex signal that is detected by the set of sensing elements of the first detection subsystem and identify, for example, a certain type of brain activity taking place in a portion of the brain pertaining to a hand of the driver 110. The processing system 125 may then communicate with the biometric sensor 115 of the second detection subsystem to obtain signals indicating a placement of the hands of the driver 110 upon the steering wheel, and/or an intensity of a hand grip of the driver 110 upon the steering wheel. The signals may be evaluated by the processing system 125 to confirm that the driver 110 is drowsy.

In some implementations, the processing system 125 may apply various levels of priorities to signals provided by various elements of the first detection subsystem and/or the second detection subsystem. In one example implementation, the application of priorities may be carried out by applying weights. For example, a greater weight may be applied to a motor cortex signal received from the headrest cortical sensor system 130 in comparison to a signal received from the imaging apparatus 105.

The imaging apparatus 105 can provide information pertaining to an eyelid status of the driver 110. Typically, continuous eyelid closure over an extended period of is a good indicator that a person is asleep. An intermittent eyelid closure may indicate that a person is drowsy. Heart rate and breathing patterns can also indicate a drowsiness state of a person. However, such states can be prone to certain ambiguities among different individuals. For example, some physical parameters (such as heart rate, breathing pattern, and/or blood pressure) of an athletic individual may be different than that of a sedentary individual.

Consequently, the processing system 125 of the driver drowsiness detection system 100 may apply a numerical weight of 8 (out of 10) for signals received from the headrest cortical sensor system 130 and use this weighting to evaluate the drowsiness state of the driver 110. The processing system 125 may apply a lower weight (5, for example) to the signals received from the imaging apparatus 105 for evaluating other physical conditions of the driver 110 to determine the drowsiness state of the driver 110.

Figure 2:
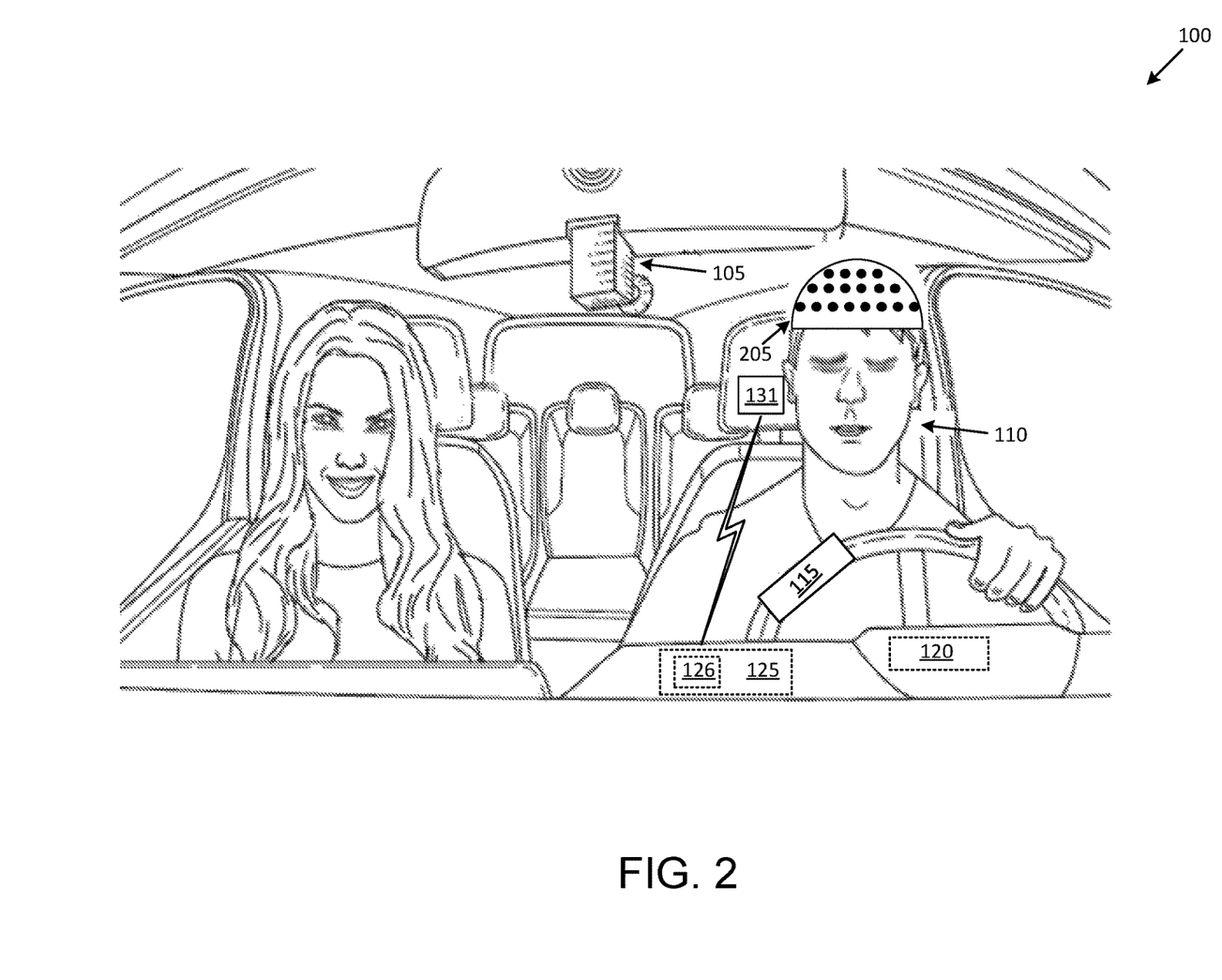
FIG. 2 illustrates an example implementation of a driver drowsiness detection system in accordance with a second embodiment of the disclosure.

FIG. 2 illustrates an example implementation of a driver drowsiness detection system 100 in accordance with a second embodiment of the disclosure. In this second embodiment, the first detection subsystem includes a brain activity monitoring element in the form of a wearable 205 incorporating a set of sensing elements. The wearable 205 can be provided in various forms such as, for example, in the form of a skullcap, a hat, a beanie, a swimming cap, or a baseball cap. Various transducers in the set of sensing elements may be arranged to detect a motor cortex signal by direct contact with the cranium of the driver 110. The wearable 205 may be communicatively coupled to the wireless transceiver 131 that communicates with the wireless transceiver 126 in the processing system 125. Operations of the various elements of the second detection subsystem such as the imaging apparatus 105, the facial recognition system 120, and the biometric sensor 115 have been described above.

Figure 3:
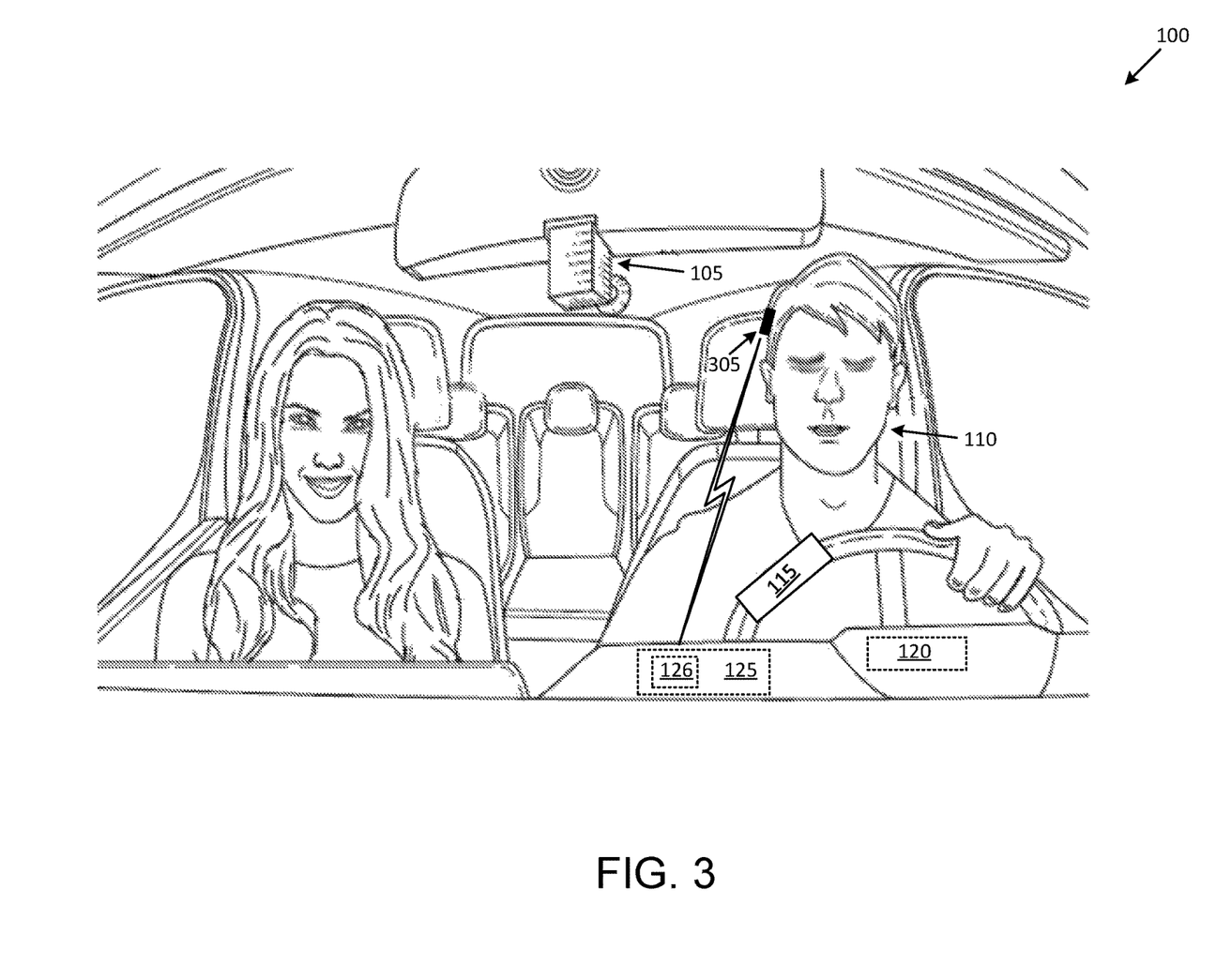
FIG. 3 illustrates an example implementation of a driver drowsiness detection system in accordance with a third embodiment of the disclosure.

FIG. 3 illustrates an example implementation of a driver drowsiness detection system 100 in accordance with a third embodiment of the disclosure. In this third embodiment, the first detection subsystem includes a brain activity monitoring element in the form of a cortical implant 305. The cortical implant 305 can include some electrodes that are surgically implanted inside the skull of the driver 110 and some other components such as a wireless transceiver, for example, that are attached to an exterior portion of the skull of the driver 110. The wireless transceiver is configured to communicate information received from the implanted electrodes, to the wireless transceiver 126 of the processing system 125.

Unlike electrodes that are implanted at certain locations of the brain for detecting brain wave patterns indicative of sleep, the electrodes of the cortical implant 305 that are inside the skull of the driver 110 are implanted at locations of the brain that are primarily associated with motor functions of various anatomical parts of the driver 110. For example, the electrodes of the cortical implant 305 may be implanted in a motor cortex portion of the brain associated with various anatomical parts of the driver 110 such as, eyes, jaw, face, lips, brows, fingers, hands, arms, and shoulder. In some implementations, one or more electrodes of the cortical implant 305 may also be placed at certain locations of the brain for detecting brain activity associated with one or more of stages of sleep.

The processing system 125 may evaluate the information provided by the electrodes of the cortical implant 305, independently, or in combination with, information provided by the second detection subsystem (imaging apparatus 105, facial recognition system 120, biometric sensor 115, etc.), and assign a sleep risk score. The sleep risk score can be assigned in a graded manner depending upon the level of drowsiness in the driver 110. For example, if the brain activity indicates that the driver 110 is beginning to drowse, the processing system 125 may assign a first numeric score. The processing system 125 may assign a second numeric score that is higher than the first numeric score, if warnings to the driver 110 go unheeded, and the driver 110 enters a sleep state.

In some other instances, one or more electrodes of the cortical implant 305 may detect an absence of brain activity associated with one or more of anatomical parts of the driver 110. For example, the absence of brain activity may indicate a lack of movement in the hands of the driver 110. Such a lack of movement may be indicative of the driver 110 failing to operate the steering wheel of the vehicle in a typical manner when driving the vehicle. The processing system 125 may evaluate additional information provided by one or more elements of the second detection subsystem, such as the biometric sensor 115, for example, and assign a sleep risk score to the driver 110. This sleep risk score can also be assigned in a graded manner as described above.

Figure 4:
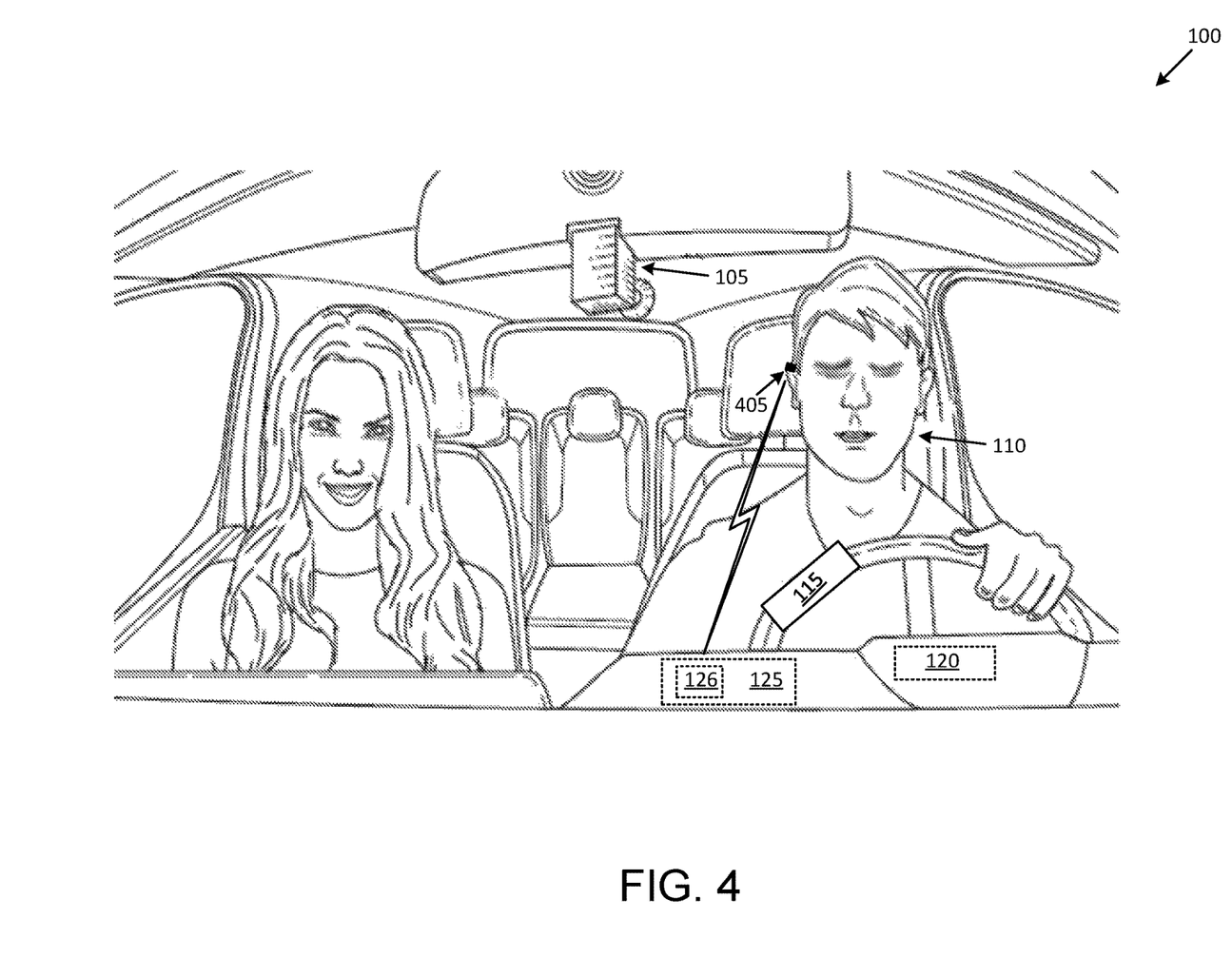
FIG. 4 illustrates an example implementation of a driver drowsiness detection system in accordance with a fourth embodiment of the disclosure.

FIG. 4 illustrates an example implementation of a driver drowsiness detection system 100 in accordance with a fourth embodiment of the disclosure. In this fourth embodiment, the first detection subsystem includes a brain activity monitoring element in the form of a motor cortex signal sensor 405 that is attached to the body of the driver 110 at one of various spots. In the example shown, the motor cortex signal sensor 405 is attached to an ear of the driver 110. In other cases, the motor cortex signal sensor 405 can be attached to other parts of the driver 110 such as the neck or the spinal cord. The motor cortex signal sensor 405 may wirelessly transmit information to the wireless transceiver 126 of the processing system 125, which evaluates the information together with information received from one or more components of the second subsystem to determine a drowsiness state of the driver 110.

Figure 5:
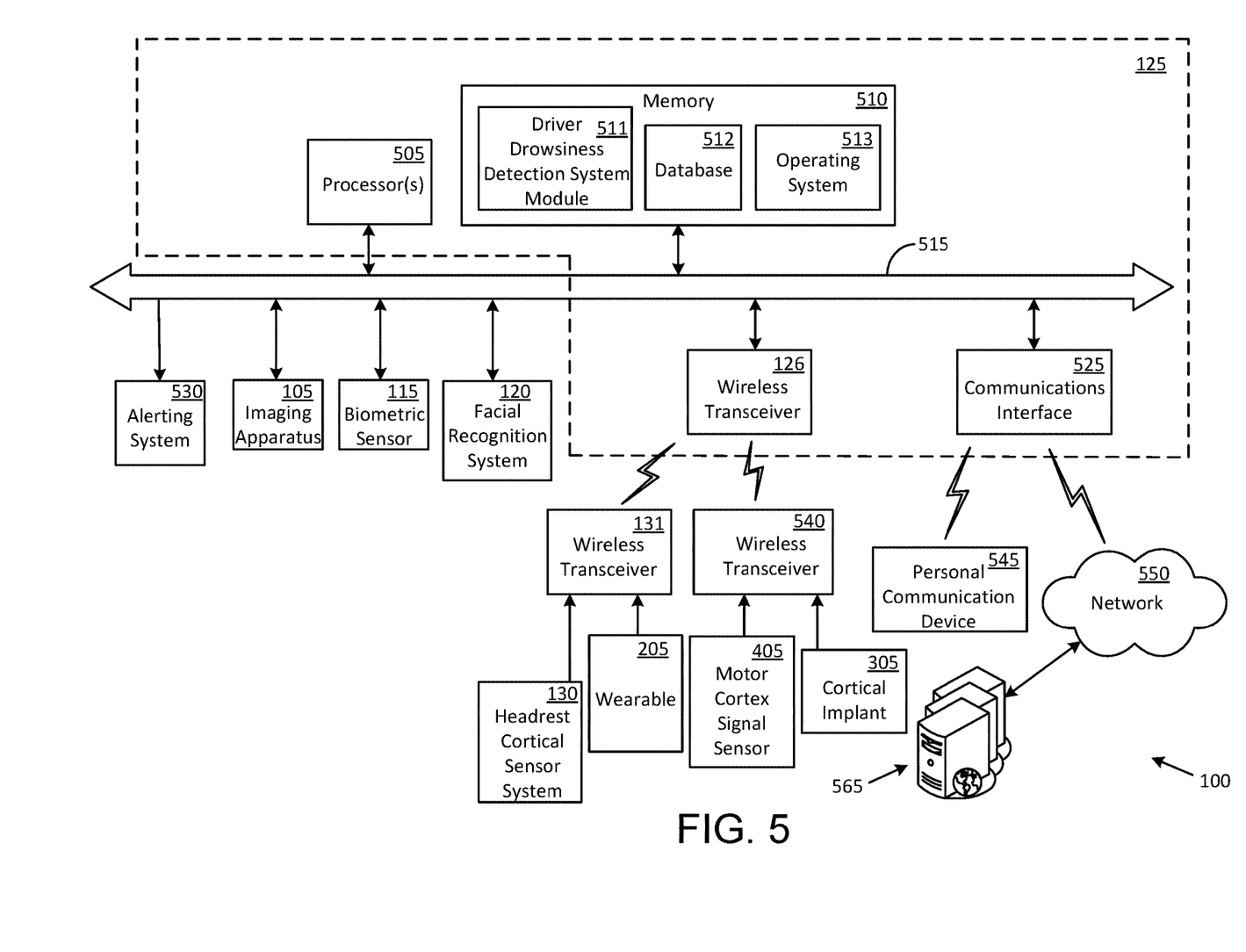
FIG. 5 shows some example components that may be included in a driver drowsiness detection system in accordance with the disclosure.

FIG. 5 shows some example components that may be included in the driver drowsiness detection system 100 in accordance with the disclosure. In this example configuration, the driver drowsiness detection system 100 may include the processing system 125, an alerting system 530, the imaging apparatus 105, the biometric sensor 115, the facial recognition system 120, and other elements that are be wirelessly coupled to the processing system 125. The various components of the driver drowsiness detection system 100 may be communicatively coupled to each other via a bus 515.

The bus 515 can be implemented using one or more of various wired and/or wireless technologies. For example, the bus can be a vehicle bus that uses a controller area network (CAN) bus protocol, a Media Oriented Systems Transport (MOST) bus protocol, and/or a CAN flexible data (CAN-FD) bus protocol. Some or all portions of the bus may also be implemented using wireless technologies such as Bluetooth®, ZigBee®, or near-field-communications (NFC), cellular, Wi-Fi, Wi-Fi direct, machine-to-machine communication, and/or man-to-machine communication to accommodate communications between the processing system 125 and various devices such as the wireless transceiver 131, a wireless transceiver 540, a personal communication device 545, and a server computer 565.

The bidirectional links between the various elements can carry commands in one direction (such as, for example, a "fetch information" command issued by the processing system 125 to the imaging apparatus 105) and can carry information in an opposite direction (such as, for example, images from the imaging apparatus 105 to the processing system 125).

The first detection subsystem can include components such as, for example, the headrest cortical sensor system 130, the wearable 205, the cortical implant 305, and the motor cortex signal sensor 405. The example components of the first detection subsystem are communicatively coupled to the wireless transceiver 126 of the processing system 125 via wireless transceivers such as the wireless transceiver 131 and the wireless transceiver 540.

The second detection subsystem can include components such as, for example, the imaging apparatus 105, the biometric sensor 115, and the facial recognition system 120. The example components of the second detection subsystem may be communicatively coupled to the processing system 125 via the bus 515.

The personal communication device 545 can be any of various devices such as, for example, a smartphone, a tablet computer, or a laptop computer. The alerting system 530 can include any of various devices such as, for example, an infotainment system in the vehicle or a horn of the vehicle. The processing system 125 can transmit an alert to the alerting system 530 and/or the personal communication device 545 to awaken the driver 110 when the driver is in a drowsy state. In some applications, the infotainment system in the vehicle and/or the personal communication device 545 may be used by the processing system 125 to execute a wakefulness test upon the driver 110.

The server computer 565 may be accessed by the processing system 125 via a communications interface 525 and a network 550 for various purposes, such as, for example, to fetch information pertaining to various operations in accordance with the disclosure. For example, the server computer 565 may provide to the processing system 125, information pertaining to processing signals for detecting drowsiness and/or for assigning sleep risk scores.

The network 550 may include any one, or a combination of networks, such as a local area network (LAN), a wide area network (WAN), a telephone network, a cellular network, a cable network, a wireless network, and/or private/public networks such as the Internet. For example, the network 550 may support communication technologies such as TCP/IP, Bluetooth, cellular, near-field communication (NFC), Wi-Fi, Wi-Fi direct, machine-to-machine communication, and/or man-to-machine communication.

The processing system 125 can include a processor 505, the wireless transceiver 126, the communications interface 525, and a memory 510. The memory 510, which is one example of a non-transitory computer-readable medium, may be used to store an operating system (OS) 513 and one or more code modules such as a driver drowsiness detection system module 511. The code modules can be provided in the form of computer-executable instructions that are executed by the processor 505 for performing various operations in accordance with the disclosure. For example, the processor 505 can execute the driver drowsiness detection system module 511 to evaluate a drowsiness state of the driver 110 and to assign a sleep rick score. The memory 510 can also include a database 512 that may be used to store information such as, for example, procedures for evaluating drowsiness and sleep risk scores of various individuals who may have operated the vehicle.

From an overall perspective of the driver drowsiness detection system 100, the processing system 125 may cooperate with various elements of the first detection subsystem and the second detection subsystem for executing various types of drowsiness detection procedures, some of which are described below.

A first drowsiness detection procedure is directed at generating a sleep prediction score based on factors such as brain engagement and sleep-versus-wakefulness brain activity. The sleep prediction score may be used as an indicator of a likelihood of the driver 110 falling into a deeper level of drowsiness or falling asleep. In one example scenario, one or more elements of the first detection subsystem may be used to detect visual and somatosensory cortex activity related to tracking objects on the road. One or more elements of the first detection subsystem may be used to detect visual and/or motor and somatosensory brain activity related to a capability of the driver 110 to interact with components of the vehicle, such as for example, the steering wheel, brakes, and accelerator.

Elements of the second detection subsystem may then be used to obtain information from the anatomical parts of the driver 110 that are associated with these activities (eyes, hand, foot, etc.). Information obtained from the elements of the first detection subsystem and elements of the second detection subsystem can then be evaluated by the processing system 125 in order to generate the sleep prediction score for the driver 110. In some cases, the sleep prediction score may be generated by combining information from one or both detection subsystems with brain wave sleep patterns indicating stage 1 of a sleep cycle.

A second drowsiness detection procedure is directed at evaluating eye-limb coordination such as, for example, maintaining a gaze with a tracked object in coordination with a movement of the head/face of the driver 110. Typically, when the driver 110 is alert, the head/face of the driver 110 will turns downwards while the line-of-sight of the eyes of the driver 110 would move upwards in order to maintain line-of-sight with the tracked object. The second drowsiness detection procedure can detect visual and somatosensory cortex activity and provide drowsiness information to the processing system 125 faster than conventional methods that determine an object tracking capability of the driver 110 based on detecting multiple movements of the head/face of the driver and eyelid status of the driver 110.

In one example implementation of the second drowsiness detection procedure, information provided to the processing system 125 by elements of the first detection subsystem is evaluated in conjunction with information derived from images provided by the imaging apparatus 105, in order to identify whether the eyes of the driver 110 are indeed tracking an object as expected. A discrepancy between the information derived from the first detection subsystem and the images provided by the imaging apparatus 105 would indicate drowsiness on the part of the driver 110. The discrepancy may, for example, be characterized by the eyes of the driver 110 failing to track an object when the head/face of the driver 110 is pointed in a different direction.

A third drowsiness detection procedure is directed at evaluating a responsiveness state of the driver 110. In this procedure, one or more elements of the first detection subsystem may be used to detect pre-motor cortex brain activity related to movement of various anatomical parts of the driver 110. For example, the first detection subsystem may be used to detect pre-motor cortex brain activity related to movement of the hands and feet of the driver 110. The brain activity may provide an indication to the processing system 125 that the driver 110 is intending to perform an action with his/her hands and/or feet upon a component of the vehicle (steering wheel and brake pedal, for example).

One or more elements of the second detection system may be used to provide information pertaining to actions carried out by the hands and/or feet of the driver 110. The information may be evaluated by the processing system 125 to detect a delay between detecting the pre-motor cortex brain activity and actions carried out by the hands and/or feet of the driver 110. The delay may be compared to a threshold time value and a sleep risk score of the driver 110 may be set accordingly. In some cases, the comparison procedure may lead to increasing a sleep risk score from a previous value to a new higher value, when the delay exceeds the threshold time value.

A fourth drowsiness detection procedure is directed at evaluating a responsiveness state of the driver 110 based on certain types of brain waves. One or more elements of the first detection subsystem may be used to quantify alpha and theta brain waves associated with wakefulness or sleepiness. Alpha waves (about 8-12 Hz neural oscillations) typically occur during wakeful relaxation with closed eyes, whereas theta waves (about 4-8 Hz neural oscillations) typically occur during descent into stage 1, non-rapid-eye-movement (non-REM) sleep. One or more elements of the second detection subsystem may be used to confirm or refute the indications provided by the elements of the first detection subsystem.

A fifth drowsiness detection procedure is generally applicable to Level 2 through Level 4 autonomous vehicles, and is directed at evaluating when, and how much, control to transfer to the autonomous vehicle based on a sleep risk score assigned to an occupant of the vehicle. Level 2 through Level 4 autonomous vehicles involve various levels of driver participation.

The Society of Automotive Engineers (SAE) defines six levels of driving automation ranging from Level 0 (fully manual) to Level 5 (fully autonomous). These levels have been adopted by the U.S. Department of Transportation. Level 0 (L0) vehicles are manually controlled vehicles having no driving related automation. Level 1 (L1) vehicles incorporate some features, such as cruise control, but a human driver retains control of most driving and maneuvering operations. Level 2 (L2) vehicles are partially automated with certain driving operations such as steering, braking, and lane control being controlled by a vehicle computer. The driver retains some level of control of the vehicle and may override certain operations executed by the vehicle computer. Level 3 (L3) vehicles provide conditional driving automation but are smarter in terms of having an ability to sense a driving environment and certain driving situations. Level 4 (L4) vehicles can operate in a self-driving mode and include features where the vehicle computer takes control during certain types of equipment failures. The level of human intervention is very low. Level 5 (L5) vehicles are fully autonomous vehicles that do not involve human participation.

The fifth drowsiness detection procedure involves the processing system 125 cooperating with an engine controller unit of an autonomous vehicle in order to vary the amount of engagement of the autonomous operating features of the autonomous vehicle. For example, in one case, the processing system 125 may evaluate a drowsiness state of the driver 110 and assign a corresponding sleep risk score. Based on the sleep risk score, the processing system 125 may provide an indication to the engine controller unit that a level of control by the driver over certain operations of the vehicle, have been compromised. The engine controller unit may respond by taking over control of these operations.

In the above disclosure, reference has been made to the accompanying drawings, which form a part hereof, which illustrate specific implementations in which the present disclosure may be practiced. It is understood that other implementations may be utilized, and structural changes may be made without departing from the scope of the present disclosure. References in the specification to "one embodiment," "an embodiment," "an example embodiment," "an example embodiment," "example implementation," etc., indicate that the embodiment or implementation described may include a particular feature, structure, or characteristic, but every embodiment or implementation may not necessarily include the particular feature, structure, or characteristic. Moreover, such phrases are not necessarily referring to the same embodiment or implementation. Further, when a particular feature, structure, or characteristic is described in connection with an embodiment or implementation, one skilled in the art will recognize such feature, structure, or characteristic in connection with other embodiments or implementations whether or not explicitly described.

Implementations of the systems, apparatuses, devices, and methods disclosed herein may comprise or utilize one or more devices that include hardware, such as, for example, one or more processors and system memory, as discussed herein. An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or any combination of hardwired or wireless) to a computer, the computer properly views the connection as a transmission medium. Transmission media can include a network and/or data links, which can be used to carry desired program code means in the form of computer-executable instructions or data structures and which can be accessed by a general purpose or special purpose computer. Combinations of the above should also be included within the scope of non-transitory computer-readable media.

Computer-executable instructions comprise, for example, instructions and data which, when executed at a processor, cause the processor to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

A memory device such as the memory 510, can include any one memory element or a combination of volatile memory elements (e.g., random access memory (RAM, such as DRAM, SRAM, SDRAM, etc.)) and non-volatile memory elements (e.g., ROM, hard drive, tape, CDROM, etc.). Moreover, the memory device may incorporate electronic, magnetic, optical, and/or other types of storage media. In the context of this document, a "non-transitory computer-readable medium" can be, for example but not limited to, an electronic, magnetic, optical, electromagnetic, infrared, or semiconductor system, apparatus, or device. More specific examples (a non-exhaustive list) of the computer-readable medium would include the following: a portable computer diskette (magnetic), a random-access memory (RAM) (electronic), a read-only memory (ROM) (electronic), an erasable programmable read-only memory (EPROM, EEPROM, or Flash memory) (electronic), and a portable compact disc read-only memory (CD ROM) (optical). Note that the computer-readable medium could even be paper or another suitable medium upon which the program is printed, since the program can be electronically captured, for instance, via optical scanning of the paper or other medium, then compiled, interpreted or otherwise processed in a suitable manner if necessary, and then stored in a computer memory.

Those skilled in the art will appreciate that the present disclosure may be practiced in network computing environments with many types of computer system configurations, including in-dash vehicle computers, personal computers, desktop computers, laptop computers, message processors, handheld devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by any combination of hardwired and wireless data links) through a network, both perform tasks. In a distributed system environment, program modules may be located in both the local and remote memory storage devices.

Further, where appropriate, the functions described herein can be performed in one or more of hardware, software, firmware, digital components, or analog components. For example, one or more application specific integrated circuits (ASICs) can be programmed to carry out one or more of the systems and procedures described herein. Certain terms are used throughout the description, and claims refer to particular system components. As one skilled in the art will appreciate, components may be referred to by different names. This document does not intend to distinguish between components that differ in name, but not function.

At least some embodiments of the present disclosure have been directed to computer program products comprising such logic (e.g., in the form of software) stored on any computer-usable medium. Such software, when executed in one or more data processing devices, causes a device to operate as described herein.

While various embodiments of the present disclosure have been described above, it should be understood that they have been presented by way of example only, and not limitation. It will be apparent to persons skilled in the relevant art that various changes in form and detail can be made therein without departing from the spirit and scope of the present disclosure. Thus, the breadth and scope of the present disclosure should not be limited by any of the above-described example embodiments but should be defined only in accordance with the following claims and their equivalents. The foregoing description has been presented for the purposes of illustration and description. It is not intended to be exhaustive or to limit the present disclosure to the precise form disclosed. Many modifications and variations are possible in light of the above teaching. Further, it should be noted that any or all of the aforementioned alternate implementations may be used in any combination desired to form additional hybrid implementations of the present disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. A method comprising:
   receiving, by a driver drowsiness detection system, a first motor cortex signal of a plurality of motor cortex signals from a brain activity monitoring element attached to a driver of a vehicle;
   identifying, by the driver drowsiness detection system and based on the first motor cortex signal, anatomical parts of the driver that are associated with a brain activity, wherein the anatomical parts of the driver comprise an eye, a face, a limb, and a torso;
   determining, by the driver drowsiness detection system, a drowsiness state of the driver by evaluating physical activity of the anatomical parts and weighting each of the plurality of motor cortex signals; and
   assigning, by the driver drowsiness detection system and based on the drowsiness state of the driver, a first sleep risk score.

2. The method of claim 1, further comprising:
   determining, by the driver drowsiness detection system, that the first motor cortex signal indicates a pre-motor cortex neural behavior of the anatomical parts of the driver; and
   evaluating, by the driver drowsiness detection system, the anatomical parts of the driver to confirm the pre-motor cortex neural behavior.

3. The method of claim 2, wherein evaluating the anatomical parts of the driver to confirm the pre-motor cortex neural behavior comprises:
   detecting, by the driver drowsiness detection system, a time delay between determining that the first motor cortex signal indicates the pre-motor cortex neural behavior and a physical action performed by one of the anatomical parts.

4. The method of claim 3, wherein the one of the anatomical parts of the driver comprises a limb of the driver.

5. The method of claim 3, further comprising:
   comparing, by the driver drowsiness detection system, the time delay to a threshold time value; and
   increasing, by the driver drowsiness detection system, the first sleep risk score to a second sleep risk score that is higher than the first sleep risk score when the time delay exceeds the threshold time value.

6. The method of claim 1, further comprising:
   determining, by the driver drowsiness detection system and based on the first motor cortex signal, a vestibulo ocular reflex capability of the driver; and
   evaluating, by the driver drowsiness detection system and based on the vestibulo ocular reflex capability, an eye-head interaction of the driver, the eye-head interaction indicating the drowsiness state of the driver.

7. The method of claim 6, wherein evaluating the eye-head interaction of the driver comprises:
   detecting, by the driver drowsiness detection system, a time delay between an eye movement and a head movement of the driver during the eye-head interaction;
   comparing, by the driver drowsiness detection system, the time delay to a threshold time value; and
   increasing, by the driver drowsiness detection system, the first sleep risk score to a second sleep risk score that is higher than the first sleep risk score when the time delay exceeds the threshold time value.

8. A method comprising:
   receiving, by a driver drowsiness detection system, a first motor cortex signal of a plurality of motor cortex signals from a brain activity monitoring element that is attached to a driver of a vehicle, wherein the drowsiness detection system is arranged to monitor an eye movement of the driver, a head movement of the driver, and a level of pressure applied by a body part of the driver on a component of the vehicle;
   detecting, by the driver drowsiness detection system, a drowsiness state of the driver by evaluating the first motor cortex signal and weighting each of the plurality of motor cortex signals;
   receiving, by the driver drowsiness detection system, a second motor cortex signal of the plurality of motor cortex signals from a drowsiness detection device placed in the vehicle; and
   confirming, by the driver drowsiness detection system, the drowsiness state of the driver by evaluating the second motor cortex signal.

9. The method of claim 8, wherein evaluating the first motor cortex signal comprises analyzing the first motor cortex signal to determine a pre-motor cortex neural behavior of anatomical parts of the driver, and wherein evaluating the second motor cortex signal comprises analyzing a physical action performed by the anatomical parts to confirm the pre-motor cortex neural behavior.

10. The method of claim 9, further comprising:
    detecting, by the driver drowsiness detection system, a time delay between determining the pre-motor cortex neural behavior of the anatomical parts and a physical action performed by the anatomical parts.

11. The method of claim 8, further comprising:
    evaluating, by the driver drowsiness detection system, the first motor cortex signal to determine a vestibule-ocular reflex capability of the driver; and
    evaluating, by the driver drowsiness detection system, an eye-head interaction of the driver based on determining the vestibule-ocular reflex capability, the eye-head interaction indicating the drowsiness state of the driver.

12. The method of claim 11, wherein evaluating the eye-head interaction of the driver comprises:
- detecting, by the driver drowsiness detection system, a time delay between an eye movement and a head movement of the driver during the eye-head interaction;
- comparing, by the driver drowsiness detection system, the time delay to a threshold time value; and
- increasing, by the driver drowsiness detection system, a first sleep risk score of the driver to a second sleep risk score of the driver when the time delay exceeds the threshold time value.

13. A system comprising:
- a brain activity monitoring element that is attached to a driver of a vehicle, the brain activity monitoring element comprising:
  - a memory that stores computer-executable instructions; and
  - a processor configured to access the memory and execute the computer-executable instructions to at least:
    - detect a brain activity by evaluating a motor cortex signal of a plurality of motor cortex signals received from the brain activity monitoring element;
    - identify anatomical parts of the driver associated with the brain activity, wherein the anatomical parts of the driver comprise an eye, a face, a limb, and a torso;
    - determine a drowsiness state of the driver by evaluating physical activity of the anatomical parts and weighting each of the plurality of motor cortex signals; and
    - generate a first sleep risk score based on the drowsiness state of the driver; and
- a drowsiness detection device placed in the vehicle for determining the drowsiness state of the driver of the vehicle, the drowsiness detection device arranged to monitor an eye movement of the driver, a head movement of the driver, and a level of pressure applied by a body part of the driver on a component of the vehicle.

14. The system of claim 13, wherein the processor is further configured to access the memory and execute additional computer-executable instructions to at least:
- determine that the first motor cortex signal indicates a pre-motor cortex neural behavior of the anatomical parts of the driver; and
- configure the drowsiness detection device to evaluate the anatomical parts of the driver for confirming the pre-motor cortex neural behavior.

15. The system of claim 14, wherein the processor is further configured to access the memory and execute additional computer-executable instructions to at least:
- detect a time delay between determining that the first motor cortex signal indicates the pre-motor cortex neural behavior and a physical action performed by the anatomical parts.

16. The system of claim 15, wherein the processor is further configured to access the memory and execute additional computer-executable instructions to at least:
- compare the time delay to a threshold time value; and
- increase the first sleep risk score to a second sleep risk score that is higher than the first sleep risk score when the time delay exceeds the threshold time value.

17. The system of claim 16, wherein the processor is further configured to access the memory and execute additional computer-executable instructions to at least:
- evaluate the first motor cortex signal to determine a vestibulo ocular reflex capability of the driver; and
- configure the drowsiness detection device to evaluate an eye-head interaction of the driver based on determining the vestibulo-ocular reflex capability, the eye-head interaction indicating the drowsiness state of the driver.

* * * * *